United States Patent

Hester, Jr.

[11] 4,000,153
[45] Dec. 28, 1976

[54] TRIAZOLOBENZODIAZEPINE INTERMEDIATES

[75] Inventor: Jackson B. Hester, Jr., Galesburg, Mich.

[73] Assignee: The Upjohn Company, Kalamazoo, Mich.

[22] Filed: Sept. 2, 1975

[21] Appl. No.: 609,445

Related U.S. Application Data

[60] Continuation of Ser. No. 509,550, Sept. 26, 1974, abandoned, which is a continuation-in-part of Ser. No. 386,088, Aug. 6, 1973, abandoned, which is a division of Ser. No. 252,504, May 11, 1972, Pat. No. 3,812,140, which is a division of Ser. No. 114,049, Feb. 9, 1971, Pat. No. 3,709,898.

[52] U.S. Cl. .................. 260/308 R; 260/283 R; 260/288 R; 260/288 CF
[51] Int. Cl.² .................................. C07D 249/08
[58] Field of Search ........................ 260/308 R

[56] References Cited
UNITED STATES PATENTS
3,709,898  1/1973  Hester ................. 260/308 R Primary Examiner—Alton D. Rollins
Attorney, Agent, or Firm—Hans L. Berneis

[57] ABSTRACT

Intermediates of the formula VI:

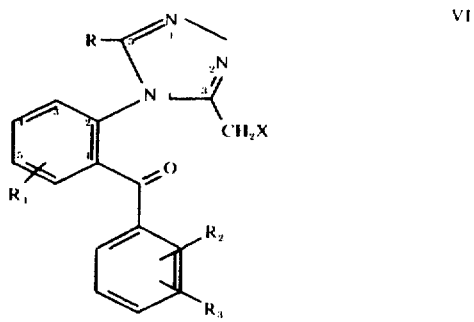

wherein R is hydrogen or alkyl of 1 to 3 carbon atoms, inclusive, wherein $R_2$ is hydrogen, fluoro, or chloro; wherein $R_3$ is hydrogen or fluoro with the proviso that $R_3$ is not fluoro, if $R_2$ is chloro; wherein $R_4$ is hydrogen, fluoro, chloro, bromo, trifluoromethyl, or nitro; and wherein X is chloro, bromo, or iodo, are produced by a multistep process. The compounds VI serve as intermediates for final compounds which are tranquilizers and sedatives and as such useful in mammals and birds.

5 Claims, No Drawings

TRIAZOLOBENZODIAZEPINE INTERMEDIATES

This application is a continuation of application Ser. No. 509,550, filed Sept. 26, 1974, now abandoned which is a continuation in part of application Ser. No. 386,088, filed Aug. 6, 1973, now abandoned which is a division of application 252,504, filed May 11, 1972, now U.S. Pat. No. 3,812,140 which is a division of application 114,049, filed Feb. 9, 1971, which is now U.S. Pat. No. 3,709,898.

BACKGROUND OF THE INVENTION

FIELD OF THE INVENTION

This invention is directed to new organic intermediate compounds and is particularly concerned with [3-(halomethyl)--H-1,2,4-triazol-4-yl]benzophenones.

The novel compounds and the process of production therefor can be illustratively represented as follows:

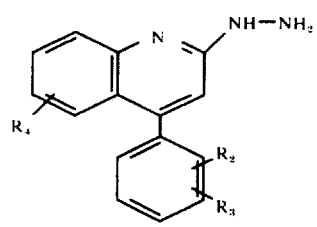

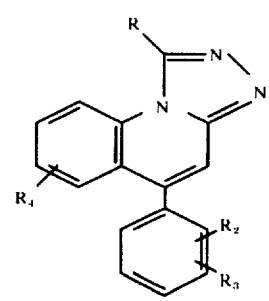

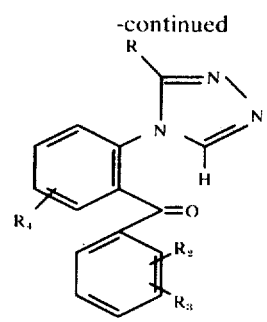

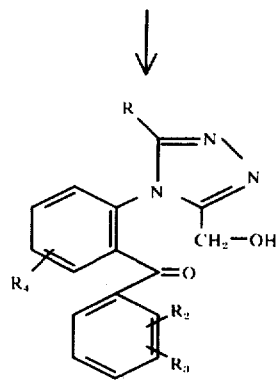

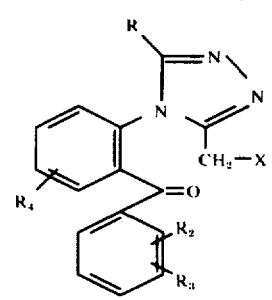

wherein R is hydrogen or alkyl of 1 to 3 carbon atoms, inclusive; wherein $R_2$ is hydrogen, fluoro, or chloro; wherein $R_3$ is hydrogen or fluoro with the proviso that $R_3$ is not fluoro, if $R_2$d is chloro; wherein $R_4$ is hydrogen, fluoro, chloro, bromo, trifluoromethyl, or nitro; and wherein X is chloro, bromo, iodo.

The more desirable products of this invention are of the formula VIA:

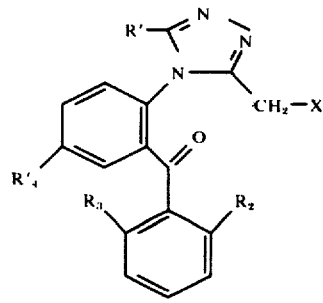

wherein R' is hydrogen or methyl; wherein $R_2$ is hydrogen, chloro, or fluoro; wherein $R_3$ is hydrogen or fluoro with the proviso that $R_3$ is not fluoro if $R_2$ is chloro; wherein $R'_4$ is hydrogen, fluoro, chloro, trifluoromethyl, and nitro; and wherein X is chloro, bromo, or iodo.

The most desirable products are of the formula VIB:

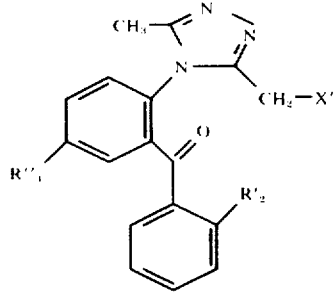

VIB wherein $R'_2$ is hydrogen or chloro; and wherein $R'_4$ is chloro or fluoro; and wherein X' is chloro or bromo.

The products of formula VI are useful per se as tranquilizers but their principal use is as intermediates for compounds of formula VII which are extremely potent tranquilizers. The compounds of formula VII are obtained from those of formula VI by the following reaction:

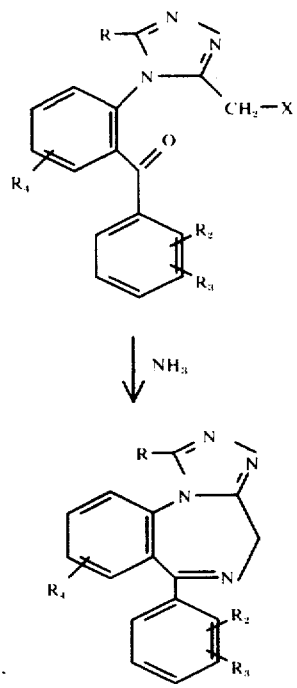

wherein R, $R_2$, $R_3$, $R_4$, and X have the same significance as above.

The process of this invention comprises:

1. Refluxing a 2-chloro-4-phenylquinoline (I) with hydrazine hydrate to give a 2-hydrazino-4-phenylquinoline (II);

2. Refluxing the 2-hydrazino-4-phenylquinoline (II) with a trialkyl orthoacylate e.g. with triethyl orthoformate, triethyl orthoacetate, triethyl orthopropionate or trimethyl orthobutyrate, in an inert organic solvent to give the corresponding 1-substituted-5-phenyl-s-triazolo-[4,3-a]quinoline (III);

3. Treating (III) with an oxidizing agent or system such as ruthenium dioxide and sodium periodate or ozone in an inert solvent at low temperature to give a mixture containing mainly a 2-(3-substituted-4H-1,2,4-triazol-4-yl)benzophenone(IV);

4. Treating (IV) with formaldehyde to obtain a 2-[3-(hydroxymethyl-5-substituted-4H-1,2,4-triazol-4-yl]benzophenone;

5. Converting alcohol V to a halide with a halogenating agent such as phosphorus tribromide, phosphorus oxychloride, phosphorus triiodide, or thionyl chloride to obtain the corresponding 2-[3-(halomethyl)-5-substituted-4H-1,2,4-triazol-4-yl]benzophenone (VI);

6. And treating (VI) with ammonia to give the corresponding end product, 1-substituted-6-phenyl-4H-s-triazolo[4,3-a]-[1,4]benzodiazepine VII.

DESCRIPTION OF THE PREFERRED EMBODIMENT

Lower alkyl groups of 1 to 3 carbon atoms, inclusive, are exemplified by methyl, ethyl, propyl, and isopropyl.

The compounds of the formulae VII including acid addition salts thereof have sedative, tranquilizing, and muscle-relaxant effects in mammals, including man and birds.

For example, sedative effects of 8-chloro-1-methyl-6-phenyl-4H-s-triazol[4,3-a][1,4]benzodiazepine are shown by the following tests in mice:

Chimney test: [Med. Exp. 4, 145 (1961)]: The effective intraperitoneal dosage for 50% of the mice ($ED_{50}$) is 0.09 mg./kg.; the oral $ED_{50}$ is 0.6 mg./kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of the test compound at which 50% of the mice remain in the dish. The $ED_{50}$ (intraperitoneal administration) in this test is 0.15 mg./kg.; the oral $ED_{50}$ is 0.045 mg./kg.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal administration) is 0.20 mg./kg.; the $ED_{50}$ (oral administration) is 0.9 mg./kg.

Nicotine antagonism test: Mice in a group of 6 are injected with the test compound (8-chloro-1-methyl-6-phenyl-4H-s-triazolo[4,3-a][1,4]benzodiazepine). Thirty minutes later the mice including control (untreated) mice are injected with nicotine salicylate (2 mg./kg.). The control mice show overstimulation, i.e., (1) running convulsions followed by (2) tonic extensor fits followed by (3) death. An intraperitoneal dosage of 0.1 mg./kg. of the test compound protected 50% of the mice against (2) and (3) ($ED_{50}$); the oral $ED_{50}$ is 0.04 mg./kg.

Antagonism to strychnine (as sulfate): The effective dosage ($ED_{50}$) of 8-chloro-1-methyl-6-phenyl-4H-s-triazolo[4,3-a][1,4]benzodiazepine is 1 mg./kg. orally in mice. The test consists in orally administering into groups of 6 mice the test compound. 8-chloro-1-methyl-6-phenyl-4H-s-triazolo[4,3-a][1,4]-benzodiazepine, and 30 minutes later 3 mg./kg. strychnine sulfate intraperitoneally. The survivors after 4 hours reflect the activity of the compound as a muslce-relaxant and antispasmodic. A dosage of 3 mg./kg. of strychnine sulfate is routinely fatal to all the control mice.

The following compounds have an (by intraperitoneal) injection) $ED_{50}$ as shown in Table I below:

TABLE I

| COMPOUND | $ED_{50}$ (in mg./kg.) | | | |
|---|---|---|---|---|
| | Ch | D | P | Ni |
| 8-chloro-1-methyl-6-(2,6-di-fluorophenyl)-4H-s-triazolo-[4,3-a][1,4]benzodiazepine | 0.009 | 0.016 | 0.020 | 0.018 |
| 8-chloro-1-ethyl-6-phenyl-4H-s-triazolo[4,3-a][1,4]benzo-diazepine | 0.8 | 0.9 | 0.9 | 0.2 |
| 8-chloro-6-phenyl-4H-s-triazolo[4,3-a][1,4]benzodiazepine | 0.25 | 0.4 | 0.7 | 0.08 |
| 8-trifluoromethyl-1-methyl-6-phenyl-4H-s-triazolo[4,3-a][1,4]benzodiazepine | 0.16 | 0.16 | 0.22 | 0.08 |
| 8-chloro-1-methyl-6-(o-chlorophenyl)-4H-s-triazolo[4,3-a][1,4]benzodiazepine | 0.05 | 0.028 | 0.045 | 0.008 |
| 8-chloro-1-methyl-6-(o-fluorophenyl)-4H-s-triazolo[4,3-a][1,4]benzodiazepine | 0.056 | 0.016 | 0.028 | 0.009 |

Ch - chimney test
D - dish test
P - pedestal test
Ni - nicotine antagonism (3) test The pharmaceutical forms of the final compounds of formula VII contemplated by this invention include pharmaceutical compositions suited for oral, parenteral and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oil, e.g., coconut oil, sesame oil, safflower oil, cottonseed oil, peanut oil may be used for preparing solutions or suspensions of the active drug. Sweetening, coloring and flavoring agents may be added.

For mammals and birds, food premixes with starch, oatmeal, dried fishmeat, fishmeal, flour and the like can be prepared.

As tranquilizers, compounds of formula VII can be used in dosages of 0.01–2.0 mg./kg. in oral or injectable preparations as described above, to alleviate tension and anxiety in mammals, or birds, such as e.g., occurs when animals are in travel.

The starting materials of formula I of this invention, substituted and unsubstituted 2-chloro-4-phenylquinolines, are partially known in the art e.g. G. A. Reynolds and C. R. Hauser, J. Am. Chem. Soc. 72, 1852 (1950) or are prepared according to the methods known in the Preparations.

In carrying out the process of the present invention, a selected 2-hydrazino-4-phenylquinoline I is heated with hydrazine hydrate. In the preferred embodiment of this invention, the reaction is carried out at the reflux temperature of the mixture, however, temperatures between 25° and 118° C. with a reaction time of 1 to 18 hours are operative. As solvents lower alkanols, e.g. methanol, ethanol, 1- and 2-propanol or excess hydrazone hydrate can be used. In the preferred embodiment of the invention, one hour of reflux of the reaction mixture under nitrogen is sufficient. At the termination of the reaction, the mixture is concentrated, poured into water and the insoluble product collected on a filter. Purification is carried out by conventional means such as extraction, chromatography or, more commonly, recrystallization to obtain the corresponding 2-hydrazino-4-phenylquinoline II.

Compound II is converted to the corresponding 1-substituted-5-phenyl-s-triazolo[4,3-a]quinoline III by heating with a lower alkanol ester of an orthocarboxylic acid, e.g. trimethyl or triethyl orthoacetate. Temperatures between 80°–170° C. are operative in this reaction. Solvents such as heptane, octane, methylcyclohexane, benzene, troluene, xylene (o, m, or p) can be used but are not necessary. In the preferred embodiment of this invention, the reaction is carried out in a nitrogen atmosphere with a higher boiling solvent e.g. xylene, at the reflux temperature of the reaction mixture. Lower alkanols, produced during the reaction by decomposition of the ortho ester, can be removed by distillation. The product III is recovered and purified by conventional procedures e.g. concentration of the reaction mixture to dryness, extraction, chromatography and/or recrystallization.

Oxidation of compound III, depending on the oxiding agent and reaction conditions used, produces 2-(3-substituted-4H-1,2,4-triazol-4-yl)benzophenone IV and/or 4-(2-benzoylphenyl)-5-substituted-4H-1,2,4-triazole-3-carboxaldehyde (IVa). The oxidation can be carried out with sodium periodate using potassium permanganate or ruthenium dioxide as catalysts or with ozone and the like. With ozone, also 1-substituted-5-phenyl-s-triazolo[4,3-a]quinolin-4(5H)-one was obtained besides compounds IV and IVa. The oxidation with ruthenium dioxide and sodium periodate is performed between zero and 30° C. for a period of 2 to 24 hours. The sodium periodate is used in excess of 5–100 times by weight compared to the weight of ruthenium dioxide. Mixtures of water and acetone are used as solvents. The reaction mixture can be filtered to recover the solid crude product or first concentrated and then filtered, and pure products can be obtained by conventional means e.g. extraction chromatography, recrystallization, combinations of these methods and the like. The reaction can also be terminated by the addition of sodium iodide and sodium thiosulfate. This method of terminating the reaction is particularly useful, if an inorganic reagent is used as oxidant. In the ozone oxidation procedure, temperatures of 0°–30° C. are used during 12 to 24 hours and a solvent or a solvent system of inert organic solvents e.g. methanol, ethanol, methylene chloride, chloroform, or a combination thereof and the like.

Compound IV is converted to the corresponding 2-[3-(hydroxymethyl)-5-substituted-4H-1,2,4-triazol-4yl]benzophenone (V) by heating it with formaldehyde in a solvent. Aqueous formaldehyde at 100°–150° for 3 to 18 hours in a sealed tube system is operative. In the preferred embodiment of this invention an excess of paraformaldehyde in an inert solvent such as toluene, xylenes, isooctane, boiling between 100°–140° C. is used. At this temperature 3 to 18 hours is sufficient for the reaction. The product, (V) is isolated and purified by conventional methods such as chromatography, extraction, recrystallization, or the like.

Compound V is converted to a 2-[3-(halomethyl)-5-substituted-4H-1,2,4-triazol-4-yl]benzophenone (VI) by treating a solution of compound V with a halogenating agent such as thionyl chloride or bromide, phosphorus oxychloride, phosphorus trichloride, tribromide, or triiodide. Inert solvents are used in this reaction e.g. benzene, toluene, methylene chloride, chloroform, carbon tetrachloride and the like. With thionyl chloride reaction temperatures of 50°—80° C. are employed, whereas with the phosphorus halides in chlorinated hydrocarbons temperatures of 0° to 25° C. are preferred. The iodide of formula VI can also be made by an exchange reaction such as treating a chloride of formula VI with sodium iodide in acetone for 2 to 18 hours at 25°–55° C. When the reaction is terminated, the products of formula VI are isolated and purified in conventional manner e.g. chromatography, extraction, recrystallization and the like.

Compound VI is cyclized to 1-substituted-6-phenyl-4H-s-triazolo[4,3-a][1,4]benzodiazepine VII by treating compound VI with a non-aqueous solution of ammonia. In the preferred embodiment of this invention tetrahydrofuran, methanol, ethanol, methylene chloride, ether and the like can be used; anhydrous ammonia without a solvent at its boiling temperature (−33° C.) can be used. In the preferred embodiment of the invention a solvent is used at a temperature between 0°–30° C. during 18–72 hours. The product is isolated and purified, at the termination of the reaction, by conventional procedures e.g. extraction, chromatography, recrystallization and the like to provide Compound VII.

The following examples are illustrative of the processes and products of the present invention, but are not to be construed as limiting.

The preparation of starting compounds I follows the following scheme:

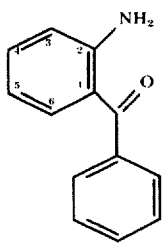
A

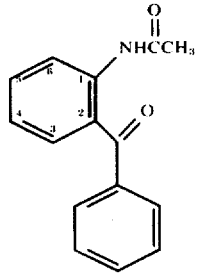
B

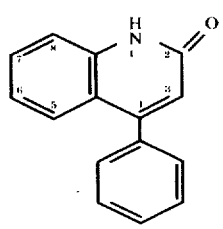
C

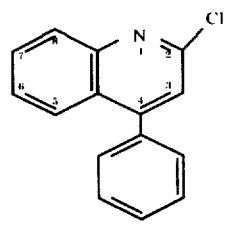
I

Preparation 1 2'-Benzoyl-4'-chloroacetanilide

Acetyl chloride (81.3 g., 1.037 mole) is added to a stirred solution of 2-amino-5-chlorobenzophenone (200.0 g., 0.864 mole) and pyridine (68.4 g., 0.864 mole) in dry ether (41.); the mixture is kept at ambient temperature for 2 hours and treated with 500 ml. of water. The layers are separated and the ether layer is dried over anhydrous sodium sulfate and concentrated. Crystallization of the residue from ethyl acetate-Skellysolve B hexane gives: 124.0 g. of 2'-benzoyl-4'-chloroacetanilide of melting point 114°–115° C. Two more crops of 2'-benzoyl-4'-chloroacetanilide are also obtained: 67.8 g. of melting point 113.5°–114.5° C. and 33.0 g. of melting point 113°–114° C.

Preparation 2 6-Chloro-4-phenyl-2(1H)-quinolone

The procedure (reaction of 2'-benzoyl-4'-chloroacetanilide with sodium hydroxide) of A. E. Drukker and C. I. Judd, J., Heterocyclic Chem. 3,359 (1966) was used for this preparation. The yield was 77%. Two other preparations have been described: S. C. Bell, T. S. Sulkowski, C. Gochman and S. J. Childress, J. Org. Chem. 27, 562 (1962); G. A. Reynolds and C. R. Hauser, J. Amer. Chem. Soc. 72, 1852 (1950).

Preparation 3 2,6-Dichloro-4-phenylquinoline

The procedure of A. E. Drukker and C. I. Judd, J. Heterocyclic Chem. 3, 359 (1966) was used (treatment of 6-chloro-4-phenyl-2(1H)quinolone with phosphorus oxychloride) for this preparation. The yield was 62%.

Using in preparation 1,2-amino-2',5-dichlorobenzophenone instead of 2-amino-5-chlorobenzophenone provides 2'-(2-chlorobenzoyl)-4'-chloroacetanilide of melting point 108°–110° C.

In similar manner using other benzophenones such as described by Fryer et al. J. Org. Chem. 30, 521 (1965); Saucy et al., Helv. Chim. Acta 45, 2226 (1962); Sternbach et al., J. Org. Chem. 20, 4488 (1961) and 27, 3781 (1962) and others, allows the preparation of 2'-(2-chlorobenzoyl)acetanilide;
2'-benzoyl-4'-nitroacetanilide;
2'-benzoyl-4'-fluoroacetanilide;
2'-benzoyl-4'-(trifluoromethyl)acetanilide;
2'-benzoyl-4'-bromoacetanilide;
2'-(2-chlorobenzoyl)-4'-nitroacetanilide;
2'-(2-chlorobenzoyl)-4'-fluoroacetanilide;
2'-(2-chlorobenzoyl)-4'-(trifluoromethyl)acetanilide
2'-(2-chlorobenzoyl)-4'-bromoacetanilide;
2'-(2,6-difluorobenzoyl)-4'-chloroacetanilide;
2'-(4-fluorobenzoyl)-4'-chloroacetanilide;
2'-(2-fluorobenzoyl)-4'-chloroacetanilide;
2'-benzoylacetanilide; and the like.

These compounds can be cyclized and halogenated like in preparations 2 and 3, to give starting compounds of formula I such as 2,6-dichloro-4-(o-chlorophenyl)quinoline;
2,6-dichloro-4-(p-fluorophenyl)quinoline;
2-chloro-6-nitro-4-phenylquinoline;
2-chloro-4-phenylquinoline;
2-chloro-6-fluoro-4-phenylquinoline;
2-chloro-6-(trifluoromethyl)-4-phenylquinoline;
2-chloro-6-bromo-4-phenylquinoline;
2-chloro-4-(2,6-difluorophenyl)quinoline;
2,6-dichloro-4-(2,6-difluorophenyl)quinoline;
2-chloro-6-fluoro-4-(o-chlorophenyl)quinoline;
2-chloro-6-nitro-4-(o-chlorophenyl)quinoline;
2-chloro-6-fluoro-4-(o-chlorophenyl)quinoline;
2-chloro-6-bromo-4-(o-chlorophenyl)quinoline;
2-chloro-6-(trifluoromethyl)-4-(o-chlorophenyl)-quinoline;
2-chloro-4-(o-chlorophenyl)quinoline; and the like.

EXAMPLE 1

6-Chloro-2-hydrazino-4-phenylquinoline

A stirred mixture of 2,6-dichloro-4-phenylquinoline (2.7 g., 0.01 mole) and hydrazine hydrate (6.8 g.) is refluxed under nitrogen for 1 hour and concentrated in vacuo. The residue is suspended in warm water, and the solid is collected by filtration, dried and recrystallized from ethyl acetate-Skellysolve B hexanes to give 1.81 g. (67% yield) of 6-chloro-2-hydrazino-4-phenylquinoline of melting point 156.5°–157° C.

Anal. calcd. for $C_{15}H_{12}ClN_3$: C, 66.79; H, 4.49; Cl, 13.15; N, 15.58. Found: C, 67.15; H, 4.65; Cl, 13.19; N, 15.32.

EXAMPLE 2

7-Chloro-1-methyl-5-phenyl-s-triazolo[4,3-a]-quinoline

A stirred mixture of 6-chloro-2-hydrazino-4-phenylquinoline (1.4 g., 0.0052 mole), triethyl orthoacetate (0.925 g., 0.0057 mole) and xylene (100 ml.) is refluxed, under nitrogen, for 2 hours 40 minutes. During this period the ethanol formed in the reaction is removed by distillation through a short, glass helix-packed column. The mixture is concentrated to dryness in vacuo and the residue is crystallized from methanol-ethyl acetate to give: 1.02 g. of 7-chloro-1-methyl-5-phenyl-s-triazolo-[4,3-a]quinoline of melting point 253.5°–255° C. and 0.26 g. of melting point 253.5–255° C. (83.9% yield). The analytical sample is crystallized from methylene chloride: methanol and has a melting point 252.5°–253.5° C.

Anal. calcd. for $C_{17}H_{12}ClN_3$: C, 69.50; H, 4.12; Cl, 12.07; N, 14.31. Found: C, 69.38; H, 4.02; Cl, 12.10; N, 14.49.

EXAMPLE 3

5-Chloro-2-(3-methyl-4H-1,2,4-triazol-4-yl)-benzophenone (Oxidation of 7-chloro-1-methyl-5-phenyl-s-triazolo[4,3-a]quinoline)

A stirred suspension of 7-chloro-1-methyl-5-phenyl-s-triazolo[4,3-a]quinoline (2.94 g., 0.01 mole) in acetone (110 ml.) is cooled in an ice-bath and treated slowly with a solution prepared by adding sodium periodate (2 g.) to a stirred suspension of ruthenium dioxide (200 mg.) in water (35 ml.). The mixture becomes dark. Additional sodium periodate (8 g.) is added during the next 15 minutes. The ice bath is removed and the mixture stirred for 45 minutes. Additional sodium periodate (4 g.) is added and the mixture is stirred at ambient temperature for 18 hours and filtered. The solid is washed with acetone and the combined filtrate is concentrated in vacuo. The residue is suspended in water and extracted with methylene chloride. The extract is dried over anhydrous potassium carbonate and concentrated. The residue is chromatographed on silica gel (100 g.) with a solution of 10% methanol and 90% ethyl acetate; 50 ml. fractions are collected. The product is eluted in fractions 10–20 and crystallized from ethyl acetate to give: 0.405 g. of melting point 168°–169.5° C. and 0.291 g. of melting point 167.5°–169° (23.4% yield) of 5-chloro-2-(3-methyl-4H-1,2,4-triazol-4-yl)benzophenone. The analytical sample has a melting point of 168° C.

Anal. calcd. for $C_{16}H_{12}ClN_3O$: C, 64.54; H, 4.06; Cl, 11.91; N, 14.11. Found: C, 64.56; H, 4.35; Cl, 11.97; 11.93; N, 14.29.

EXAMPLE 4

5-Chloro-2-[3-(hydroxymethyl)-5-methyl-4H-1,2,4-triazol-4-yl]benzophenone

A stirred mixture of 5-chloro-2-(3-methyl-4H-1,2,4-triazol-4-yl)benzophenone, (2.98 g., 0.01 mole) paraformaldehyde (3 g.) and xylene (100 ml.) is warmed under nitrogen, in a bath maintained at 125° C. for 7 hours. The mixture is then concentrated in vacuo. The residue is chromotagraphed on silica gel (150 g.) with 3% methanol 97% chloroform. Fifty-ml. fractions are collected. The product is eluted in fractions 20–44. The fractions are concentrated and the residue is crystallized from ethanolethyl acetate to give: 1.64 g. of 5-chloro-2-[3-(hydroxymethyl)-5-methyl-4H-1,2,4-triazol-4-yl]benzophenone of melting point 138°–142°C.; 0.316 g. of melting point 138.5°–141°C.; 0.431 g. of melting point 139°–141°C. (a total yield of 72.8%). The analytical sample has a melting point of 138°–139°C.

Anal. calcd. for $C_{17}H_{14}ClN_3O_2$:
C, 62.30; H, 4.30; Cl, 10.81; N, 12.82. Found: C, 62.23; H, 4.22; Cl, 10.82; N, 11.73.

EXAMPLE 5

5-Chloro-2-[3-(bromomethyl)-5-methyl-4H-1,2,4-triazol-4-yl]benzophenone

A solution of 5-chloro-2-[3-(hydroxymethyl)-5-methyl-4H-1,2,4-triazol-4-yl]benzophenone (328 mg., 0.001 mole) in dry, hydrocarbon-stabilized chloroform (5 ml.) is cooled in an ice bath and treated with phosphorus tribromide (0.1 ml.). The colorless solution is kept in the ice bath for 55 minutes, and then at ambient temperature (22°–24° C.), for 5 hours. The resulting yellow solution is poured into a mixture of ice and dilute sodium bicarbonate. This mixture is extracted with chloroform. The extract is washed with brine, dried over anhydrous magnesium sulfate and concentrated. The residue is crystallized from methylene chloride-ethyl acetate to give: 0.285 g. of 5-chloro-2-[3-(bromomethyl)-5-methyl-4H-1,2,4-triazol-4-yl]benzophenone of melting point 200°–240°(decomposition) and 0.030 g. of melting point 200°–240° (decomposition) and 0.030 g. of melting point 200°–220° C. (decomposition). The analytical sample has a melting point of 200°–240° C. (decomposition).

Anal. calcd. for $C_{17}H_{13}BrClN_3O$:

C, 52.26; H, 3.35; Br, 20.46; Cl, 9.08; N, 10.76. Found: C, 52.13, 52.45; H, 3.77, 3.66; Br, 20.44; Cl, 9.20; N, 10.43.

EXAMPLE 6

5-Chloro-2-[3-(chloromethyl)-5-methyl-4H-1,2,4-triazol-4-yl]benzophenone

A solution of 5-chloro-2-[3-(hydroxymethyl)-5-methyl-4H-1,2,4-triazol-4-yl]benzophenone (328 mg., 0.001 mole) in thionyl chloride (2 ml.) is warmed during 40 minutes to a bath temperature of 78° C. and kept at 78°–83° C. for 1 hour 25 minutes. It is then cooled and poured into ice water. This mixture is neutralized with sodium bicarbonate and extracted with chloroform. The extract is washed with brine, dried over anhydrous magnesium sulfate and concentrated in vacuo. The residue is crystallized from ethyl acetate Skellysolve B hexanes to give: 0.240 g. of melting point 144.5°–147° C. and 0.045 g. of melting point 144.5°–146.5° C. of 5-chloro-2-[3-(chloromethyl)-5-methyl-4H-1,2,4-triazol-4-yl]benzophenone. The analytical sample has a melting point of 139°–140° C.

Anal. calcd. for $C_{17}H_{13}Cl_2N_3O$:

C, 58.96; H, 3.78; Cl, 20.48; N, 12.14. Found: C, 59.22; H, 3.80; Cl, 20.66; N, 11.91.

EXAMPLE 7

5-Chloro-2-[3-(iodomethyl)-5-methyl-4H-1,2,4-triazol-4-yl]benzophenone

5-Chloro-2-[3-(chloromethyl)-5-methyl-4H-1,2,4-triazol-4-yl]benzophenone (346 mg. 0.001 mole) is added to a stirred solution of sodium iodide (300 mg., 0.002 mole) in acetone, and the resulting mixture is stirred at ambient temperature for 6 hours 45 minutes and poured into ice water. This mixture is extracted with chloroform. The extract is washed with brine, dried and concentrated. The residue is crystallized from methylene chloride-ethyl acetate to give: 0.227 g. of 5-chloro-2-[3-(iodomethyl)-5-methyl-4H-1,2,4-triazol-4-yl]benzophenone of melting point 185.5°–188.5° C. (decomposition). The analytical sample has a melting point of 185°–200°C. (decomposition).

Anal. calcd. for $C_{17}H_{13}ClIN_3O$:

C, 46.65; H, 2.99; cl, 8.10; I, 29.00; N, 9.60. Found: C, 46.78; H, 2.88; cl, 8,59; I, 26.98; N, 9.23.

EXAMPLE 8

8-Chloro-1-methyl-6-phenyl-4H-s-triazolo[4,3-a]-[1,4]benzodiazepine

A stirred suspension of 5-chloro-2-[3-(bromomethyl)-5-methyl-4H-1,2,4-triazol-4-yl]benzophenone (391 mg., 0.001 mole) in tetrahydrofuran (15 ml.) is cooled in an ice bath and treated with a saturated solution of ammonia in methanol (12.5 ml.). The resulting solution is allowed to warm to ambient temperature and stand for 24 hours. It is then concentrated in vacuo. The residue is suspended in water, treated with a little sodium bicarbonate and extracted with methylene chloride. The extract is washed with brine, dried with anhydrous potassium carbonate and concentrated. The residue is crystallized from methylene chloride-ethyl acetate to give 0.220 g. of crude product of melting point 227°–228.5° C. Recrystallization of this material from ethyl acetate gives 0.141 g. of 8-chloro-1-methyl-6-phenyl-4H-s-triazolo[4,3-a][1,4]benzodiazepine of melting point 228°–229.5° C., 0.053 g. of melting point 228.5°–229.5° C. and 0.021 g. of melting point 228°–229.5° C.

Reaction of the 5-chloro-2-[3-(chloromethyl)-5-methyl-4H-1,2,4-triazol-4-yl]benzophenone with ammonia in methanol also gives 8-chloro-1-methyl-6-phenyl-4H-s-triazolo[4,3-a]-[1,4]benzodiazepine, but the reaction is slower. It requires more than 2 days to go to completion.

In like manner, 782 mg. (0.002 mole) of 5-chloro-2-[3-(bromomethyl)-5-methyl-4H-1,2,4-triazol-4-yl]benzophenone in methylene chloride cooled in a dry ice-methanol bath gives with anhydrous ammonia 515 mg. of 8-chloro-1-methyl-6-phenyl-4H-s-triazolo[4,3-a][1,4]benzodiazepine of melting point 226°–227° C.

EXAMPLE 9

6-Chloro-4-(2,6-difluorophenyl)-2-hydrazinoquinoline

In the manner given in Example 1, 2,6-dichloro-4-(2,6-difluorophenyl)quinoline is reacted at reflux with hydrazine hydrate to give 6-chloro-4-(2,6-difluorophenyl)-2-hydrazinoquinoline.

EXAMPLE 10

7-Chloro-1-methyl-5-(2,6-difluorophenyl)-s-triazolo[4,3a]quinoline

In the manner given in Example 2, 6-chloro-4-(2,6-difluorophenyl)-2-hydrazinoquinoline and triethyl orthoacetate are refluxed in xylene to give 7-chloro-1-methyl-5-(2,6-difluorophenyl)-s-triazolo[4,3-a]quinoline.

EXAMPLE 11

5-Chloro-2',6'-difluoro-2-(3-methyl-4H-1,2,4-triazol-4-yl)benzophenone

In the manner given in Example 3, 7-chloro-1-methyl-5-(2,6-difluorophenyl)-s-triazolo[4,3-a]quinoline is oxidized at low temperature with sodium periodate and ruthenium dioxide to give 5-chloro-2',6'-difluoro-2-(3-methyl-4H-1,2,4-triazol-4yl)benzophenone.

EXAMPLE 12

5-Chloro-2',6'-difluoro-2-[3-(hydroxymethyl)-5-methyl-4H-1,2,4-triazol-4-yl]benzophenone In the manner given in Example 4, 5-chloro-2',6'-difluoro-2-(3-methyl-4H-1,2,4-triazol-4-yl)benzophenone is heated with paraformaldehyde in xylene at 125° C. to give 5-chloro-2',6'-difluoro-2-[3-(hydroxymethyl)-5-methyl-4H-1,2,4-triazol-4-yl]benzophenone.

EXAMPLE 13

5-Chloro-2',6'-difluoro-2-[3-(bromomethyl)-5-methyl-4H-1,2,4-triazol-4-yl]benzophenone In the manner given in Example 5, 5-chloro-2',6'-difluoro-2-[3-(hydroxymethyl)-5-methyl-4H-1,2,4-triazol-4-yl]benzophenone is treated with phosphorus tribromide to give 5-chloro-2',6'-difluoro-2-[3-(bromomethyl)-5-methyl-4H-1,2,4-triazol-4-yl]benzophenone.

EXAMPLE 14

8-Chloro-1-methyl-6-(2,6-difluorophenyl)-4H-s-triazolo[4,3-a][1,4]benzodiazepine In the manner given in Example 8, 5-chloro-2',6'-difluoro-2-[3-(bromomethyl)-5-methyl-4H-1,2,4-triazolo-4-yl]benzophenone was reacted with a saturated solution of ammonia in methanol to give 8-chloro-1-methyl-6-(2,6-difluorophenyl)-4H-s-triazolo[4,3-a][1,4]benzodiazepine of melting point 126°–127° C.

EXAMPLE 15

6-Chloro-4-(o-chlorophenyl)-2-hydrazinoquinoline

In the manner given in Example 1, 2,6-dichloro-4-(o-chlorophenyl)quinoline is reacted at reflux with hydrazine hydrate to give 6-chloro-4-(o-chlorophenyl)-2-hydrazinoquinoline.

EXAMPLE 16

7-Chloro-1-methyl-5-(o-chlorophenyl)-s-triazolo[4,3-a]quinoline

In the manner given in Example 2, 6-chloro-4-(o-chlorophenyl)-2-hydrazinoquinoline and triethyl orthoacetate are refluxed in xylene to give 7-chloro-1-methyl-5-(o-chlorophenyl)-s-triazolo[4,3-a]quinoline of melting point 257°–259° C.

EXAMPLE 17

2',5-Dichloro-2-(3-methyl-4H-1,2,4-triazol-4-yl)benzophenone

In the manner given in Example 3, 7-chloro-1-methyl-5-(o-chlorophenyl)-s-triazolo[4,3-a]quinoline is oxidized at low temperature with sodium periodate with ruthenium dioxide to give 2',5-dichloro-2-(3-methyl-4H-1,2,4-triazol-4-yl)benzophenone of melting point 147.5°–148.5° C.

EXAMPLE 18

2',5-Dichloro-2-[3-(hydroxymethyl)-5-methyl-4H-1,2,4-triazol-4-yl]benzophenone

In the manner given in Example 4, 2',5-dichloro-2-(3-methyl-4H-1,2,4-triazol-4-yl)benzophenone is heated with paraformaldehyde in xylene at 125° C. to give 2',5-dichloro-2-[3-(hydroxymethyl)-5-methyl-4H-1,2,4-triazol-4-yl]benzophenone of melting point 193.5°–195° C.

EXAMPLE 19

2',5-Dichloro-2-[3-(bromomethyl)-5-methyl-4H-1,2,4-triazol-4-yl]benzophenone

In the manner given in Example 5, 2',5-dichloro-2-[3-(hydroxymethyl)-5-methyl-4H-1,2,4-triazol-4-yl]benzophenone is treated with phosphorus tribromide to give 2',5-dichloro-2-[3-(bromomethyl)-5-methyl-4H-1,2,4-triazol-4-yl]benzophenone.

EXAMPLE 20

2',5-Dichloro-2-[3-(chloromethyl)-5-methyl-4H-1,2,4-triazol-4-yl]benzophenone

In the manner given in Example 6, 2',5-dichloro-2-[3-(hydroxymethyl)-5-methyl-4H-1,2,4-triazol-4-yl]benzophenone is warmed with thionylchloride to give 2',5-dichloro-2-[3-(chloromethyl)-5-methyl-4H-1,2,4-triazol-4-yl]benzophenone of melting point 127°–130° C.

EXAMPLE 21

2',5-Dichloro-2-[3-(iodomethyl)-5-methyl-4H-1,2,4-triazol-4-yl]benzophenone

In the manner given in Example 7, 2',5-dichloro-2-(chloromethyl)-5-methyl-4H-1,2,4-triazol-4-yl]benzophenone is treated with potassium iodide in acetone to give 2',5-dichloro-2-[3-(iodomethyl)-5-methyl-4H-1,2,4-triazol-4-yl]benzophenone of melting point 185°–195° C. (decomposition).

EXAMPLE 22

8-Chloro-1-methyl-6-(o-chlorophenyl)-4H-s-triazolo[4,3-a][1,4]benzodiazepine

In the manner given in Example 8, 2',5-dichloro-2-[3-(bromomethyl)-5-methyl-4H-1,2,4-triazol-4-yl]benzophenone is reacted with a saturated solution of ammonia in methanol to give 8-chloro-1-methyl-6-(o-chlorophenyl)-4H-s-triazolo-[4,3-a][1,4]benzodiazepine of melting point 225°–228° C.

EXAMPLE 23

6-Nitro-4-(o-chlorophenyl)-2-hydrazinoquinoline

In the manner given in Example 1, 2-chloro-6-nitro-4-(o-chlorophenyl)quinoline is reacted at reflux with hydrazine hydrate to give 6-nitro-4-(o-chlorophenyl)-2-hydrazinoquinoline.

EXAMPLE 24

7-Nitro-1-methyl-5-(o-chlorophenyl)-s-triazolo [4,3-a]quinoline

In the manner given in Example 2, 6-nitro-4-(o-chlorophenyl)-2-hydrazinoquinoline, and triethyl orthoacetate are refluxed in xylene to give 7-nitro-1-methyl-5-(o-chlorophenyl)-s-triazolo[4,3-a]quinoline.

EXAMPLE 25

2'-Chloro-5-nitro-2-(3-methyl-4H-1,2,4-triazol-4-yl)benzophenone

In the manner given in Example 3, 7-nitro-1-methyl-5-(o-chlorophenyl)-s-triazolo[4,3-a]quinoline is oxidized at low temperature with sodium periodate with ruthenium dioxide to give 2'-chloro-5-nitro-2-(3-methyl-4H-1,2,4-triazol-4-yl)benzophenone.

EXAMPLE 26

2'-Chloro-5-nitro-2-[3-(hydroxymethyl)-5-methyl-4H-1,2,4-triazol-4-yl]benzophenone In the manner given in Example 4, 2'-chloro-5-nitro-2-(3-methyl-4H-1,2,4-triazol-4-yl)benzophenone is heated with paraformaldehyde at 125° C. to give 2'-chloro-5-nitro-2-[3-(hydroxymethyl)-5-methyl-4H-1,2,4-triazol-4-yl]benzophenone.

EXAMPLE 27

2'-Chloro-5-nitro-2-[3-(bromomethyl)-5-methyl-4H-1,2,4-triazol-4-yl]benzophenone In the manner given in Example 5, 2'-chloro-5-nitro-2-[3-(hydroxymethyl)-5-methyl-4H-1,2,4-triazol-4-yl]-benzophenone is treated with phosphorus tribromide to give 2'-chloro-5-nitro-2-[3-(bromomethyl)-5methyl-4H-1,2,4-triazol-4-yl]benzophenone.

EXAMPLE 28

8-Nitro-1methyl-(o-chlorophenyl)-4H-s-triazolo-[4,3-a][1,4]benzodiazepine

In the manner given in Example 8,2'-chloro-5nitro-2-[3-(bromomethyl)-5-methyl-4H-1,2,4-triazol-4-yl]benzophenone is reacted with a saturated solution of ammonia in methanol to give 8-nitro-1-methyl-6-(o-chlorophenyl)-4H-s-triazolo- [4,3-a][1,4]benzodiazepine of melting point 231°–233° C.

EXAMPLE 29

6-Fluoro-4-(o-chlorophenyl)-2-hydrazinoquinoline

In the manner given in Example 1, 2-chloro-6-fluoro-4-(o-chlorophenyl)quinoline is reacted with hydrazine hydrate at reflux to give 6-fluoro-4-(o-chlorophenyl)-2hydrazino- quinoline.

EXAMPLE 30

7-Fluoro-1-methyl-5-(o-chlorophenyl)-s-triazolo[4,3-a]quinoline

In the manner given in Example 2, 6-fluoro-4-(o-chlorophenyl)-2-hydrazinoquinoline and triethyl orthoacetate are refluxed in xylene to give 7-fluoro-1-methyl-5-(o-chlorophenyl)-s-triazolo[4,3-a]quinoline.

EXAMPLE 31

2'-Chloro-5-fluoro-2-(3-methyl-4H-1,2,4-triazol-4-yl) benzophenone

In the manner given in Example 3, 7-fluoro-1-methyl-5-(o-chlorophenyl)-s-triazolo[4,3-a]quinoline is oxidized at low temperature with sodium periodate and ruthenium dioxide to give 2'-chloro-5-fluoro-2-(3-methyl-4H-1,2,4-triazol-4-yl)benzophenone

EXAMPLE 32

2'-Chloro-5-fluoro-2-[3-(hydroxymethyl)-5-methyl-4H-1,2,4-triazol-4-yl]benzopheone In the manner given in Example 4, 2'-chloro-5-fluoro- 2-(3-methyl-4H-1,2,4-triazol-4-yl)benzophenone paraformaldehyde and xylene are warmed under nitrogen to about 122° C. to give 2'-chloro-5-fluoro-2-[3-(hydroxymethyl)-5-methyl-4H-1,2,4-triazol-4-yl]benzophenone.

EXAMPLE 33

2'-Chloro-5-fluoro-2-[3-(bromomethyl)-5-methyl-4H-1,2,4-triazol-4-yl]benzophenone In the manner given in Example 5, 2'-chloro-5-fluoro- 2-[3-(hydroxymethyl)-5methyl-b 4H-1,2,4-triazol-4-yl]-benzophenone is treated with phosphorus tribromide in chloroform to give 2'-chloro-5-fluoro-2-[3-(bromomethyl)-5-methyl-4H-1,2,4-triazol-4-yl]benzophenone.

EXAMPLE 34

6-(Trifluoromethyl)-4-(o-chlorophenyl)-2-hydrazinoquinoline

In the manner given in Example 1, 2-chloro-6-(trifluromethyl)-4-(o-chlorophenyl)quinoline is reacted with hydrazine hydrate at reflux to give 6-(trifluoromethyl)- 4-(o-chlorophenyl)-2-hydrazinoquinoline.

EXAMPLE 35

7-(Trifluoromethyl)-1-methyl-5-(o-chlorophenyl)-s-triazolo[4,3-a]quinoline

In the manner given in Example 2, 6-(trifluoromethyl)-4-(o-chlorophenyl)-2-hydrazinoquinoline and triethylorthoaceate are refluxed in xylene to give 7-(trifluoromethyl)-1-methyl-5-(o-chlorophenyl)-s-triazolo[4,3-a]- quinoline.

EXAMPLE 36

2'-Chloro-5-(trifluoromethyl)-2-(3-methyl-4H-1,2,4-triazol-4-yl)benzophenone

In the manner given in Example 3, 7-(trifluoromethyl)-1-methyl-5-(o-chlorophenyl)-s-triazolo[4,3-a]quinoline is oxidized at low temperature with sodium periodate and ruthenium dioxide to give 2'-chloro-5-(trifluoromethyl)-2-(3-methyl-4H-1,2,4-triazol-4-yl)benzophenone.

EXAMPLE 37

2-Chloro-5-(trifluoromethyl)-2-[3-(hydroxymethyl)-5-methyl-4H-1,2,4-triazol-4-yl]benzophenone In the manner given in Example 4, 2'-chloro-5-(trifluoromethyl)-2-(3-methyl-4H-1,2,4-triazol-4-yl)benzophenone, paraformaldehyde and xylene are warmed under nitrogen to about 122° C. to give 2'-chloro-5-trifluoromethyl)-2-[3-(hydroxymethyl)-5-methyl-4H-1,2,4-triazol-4-yl]benzophenone.

EXAMPLE 38

2'-Chloro-5-(trifluoromethyl)-2-[3-(bromomethyl)-5-methyl-4H-1,2,4-triazol-4yl]benzophenone In the manner given in Example 5, 2'-chloro-5-(trifluromethyl)-2-[3-(hydroxymethyl)-5-methyl-4H-1,2,4-triazol-4-yl]benzophenone is treated with phosphorus tribromide in chloroform to give 2'-chloro-5-(trifluoromethyl)-2-[3-(bromomethyl)-5-methyl-4H-1,2,4-triazol-4-yl]- benzophenone.

EXAMPLE 39

4-(o-chlorophenyl)-2-hydrazinoquinoline

In the manner given in Example 1, 2-chloro-4-(o-chlorophenyl)quinoline is reacted with hydrazine hydrate at reflux to give 4-(o-chlorophenyl)-2-hydrazinoquinoline.

EXAMPLE 40

1-methyl-5-(o-chlorophenyl)-s-triazolo[4,3-a]-quinoline

In the manner given in Example 2, 4-(o-chlorophenyl)-2-hydrazinoquinoline and triethyl orthoacetate are refluxed in xylene to give 1-methyl-5-(o-chlorophenyl)-s-triazolo[4,3-a]quinoline.

EXAMPLE 41

2'-Chloro-2-(3-methyl-4H-1,2,4-triazol-4-yl)-benzophenone

In the manner given in Example 3, 1-methyl-5-(o-chlorophenyl)-s-triazolo[4,3-a]quinoline is oxidized at low temperature with sodium periodate and ruthenium dioxide to give 2'-chloro-2-(3-methyl-4H-1,2,4-triazol-4-yl)benzophenone.

EXAMPLE 42

2'-Chloro-2-[3-(hydroxymethyl)-5-methyl-4H-1,2,4-triazol-4-yl]benzophenone

In the manner given in Example 4, 2'-chloro-2-(3-methyl-4H-1,2,4-triazol-4-yl)benzophenone, paraformaldehyde and xylene are warmed under nitrogen to about 122° C. to give 2'-chloro-2-[3-(hydroxymethyl)-5-methyl-4H-1,2,4-triazol-4-yl]benzophenone.

EXAMPLE 43

2-Chloro-2-[3-(bromomethyl)-5-methyl-4H-1,2,4-triazol-4-yl]benzophenone

In the manner given in Example 5, 2'-chloro-2-[3-(hydroxymethyl)-5-methyl-4H-1,2,4-triazol-4-yl]benzophenone is treated with phosphorus tribromide in chloroform to give 2'-chloro-2-[3-(bromomethyl)-5-methyl-4H-1,2,4-triazol-4yl]benzophenone.

EXAMPLE 44

6-Chloro-4-(o-fluorophenyl)-2-hydrazinoquinoline

In the manner given in Example 1, 2,6-dichloro-4-(o-fluorophenyl)quinoline is reacted with hydrazine hydrate at reflux to give 6-chloro-4-(o-fluorophenyl)-2-hydrazinoquinoline.

EXAMPLE 45

7-Chloro-1-methyl-5-(o-fluorophenyl)-s-triazolo[4,3-a]quinoline

In the manner given in Example 2, 6-chloro-4-(o-fluorophenyl)-2-hydrazinoquinoline and triethyl orthoacetate are refluxed in xylene to give 7-chloro-1-methyl-5-(o-fluorophenyl)-s-triazolo[4,3-a]quinoline.

EXAMPLE 46

2'-fluoro-5-chloro-2-(3-methyl-4H-1,2,4-triazol-4yl)benzophenone

In the manner given in Example 3, 7-chloro-1-methyl-5-(o-fluorophenyl)-s-triazolo[4,3-a]quinoline is oxidized at low temperature with sodium periodate and ruthenium dioxide to give 2'-fluoro-5-chloro-2-(3-methyl-4H-1,2,4-triazol-4-yl)benzophenone.

EXAMPLE 47

2'-Fluoro-5-chloro-2-[3-(hydroxymethyl)-5-methyl-4H-1,2,4-triazol-4-yl]benzophenone In the manner given in Example 4, 2'-fluoro-5-chloro-2-(3-methyl-4H-1,2,4-triazol-4-yl)benzophenone, paraformaldehyde and xylene are warmed under nitrogen to about 122° C. to give 2'-fluoro-5-chloro-2-[3-(hydroxymethyl)-5-methyl-4H-1,2,4-triazol-4-yl]benzophenone.

EXAMPLE 48

2'-Fluoro-5-chloro-2-[3-(bromomethyl)-5-methyl-4H-1,2,4-triazol-4-yl]benzophenone In the manner given in Example 5, 2'-fluoro-5-chloro-2-[3-(hydroxymethyl)-5-methyl-4H-1,2,4-triazol-4-yl]-benzophenone is treated with phosphorus tribromide in chloroform to give 2'-fluoro-5-chloro-2-[3-(bromomethyl)-5-methyl-4H-1,2,4-triazol-4-yl]benzophenone.

EXAMPLE 49

6-Bromo-4-phenyl-2-hydrazinoquinoline

In the manner given in Example 1, 2-chloro-6-bromo-4-phenylquinoline is reacted with hydrazine hydrate at reflux to give 6-bromo-4-phenyl-2-hydrazinoquinoline.

EXAMPLE 50

7-Bromo-1-methyl-5-phenyl-s-triazolo[4,3-a]-quinoline

In the manner given in Example 2, 6-bromo-4-phenyl-2-hydrazinoquinoline and triethyl orthoacetate are refluxed in xylene to give 7-bromo-1-methyl-5-phenyl-s-triazolo[4,3-a]quinoline.

EXAMPLE 51

5-Bromo-2-(3-methyl-4H-1,2,4-triazol-4-yl)benzophenone

In the manner given in Example 3, 7-bromo-1-methyl-5-phenyl-s-triazolo[4,3-a]quinoline is oxidized at low temperature with sodium periodate and ruthenium dioxide to give 5-bromo-2-(3-methyl-4H-1,2,4-triazol-4-yl)benzophenone.

EXAMPLE 52

5-Bromo-2-[3-(hydroxymethyl)-5-methyl-4H-1,2,4-triazol-4-yl]benzophenone

In the manner given in Example 4, 5-bromo-2-(3-methyl-4H-1,2,4-triazol-4-yl)benzophenone, paraformaldehyde and xylene is warmed under nitrogen to about 122° C. to give 5-bromo-2-[3-(hydroxymethyl)-5-methyl-4H-1,2,4-triazol-4-yl]benzophenone.

EXAMPLE 53

5-Bromo-2-[3-(bromomethyl)-5-methyl-4H-1,2,4-triazol-4-yl]benzophenone

In the manner given in Example 5, 5-bromo-2-[3-(hydroxymethyl)-5-methyl-4H-1,2,4-triazol-4-yl]benzophenone is treated with phosphorus tribromide in chloroform to give 5-bromo-2-[3-(bromomethyl)-5-methyl-4H-1,2,4-triazol-4-yl]benzophenone.

In the manner given in the preceding Example, other 2-(3-halomethyl-4H-1,2,4-triazol-4-yl)benzophenones of forumla VI can be synthesized. Representative compounds thus obtained include:

2'-chloro-2-[3-(chloromethyl)-5-methyl-4H-1,2,4-triazol-4-yl]benzophenone;
2',5-dichloro-2-[3-(bromomethyl)-4H-1,2,4-triazol-4-yl]-benzophenone;
6-bromo-2-[3-(iodomethyl)-5-methyl-4H-1,2,4-triazol-4-yl]-benzophenone;
2'-chloro-5-bromo-2-[3-(chloromethyl)-5-methyl-4H-1,2,4-triazol-4-yl]benzophenone;
2'-chloro-5-(trifluoromethyl)-2-[3-(bromomethyl)-4H-1,2,4-triazol-4-yl]benzophenone;
2',6'-difluoro-2-[3-(chloromethyl)-5-methyl-4H-1,2,4-triazol-4-yl]benzophenone;
4-chloro-2'-fluoro-2-[3-(bromomethyl)-5-methyl-4H-1,2,4-triazol-4-yl]benzophenone;
3-nitro-3'-chloro-2-[3-(bromomethyl)-5-methyl-4H-1,2,4-triazol-4-yl]benzophenone;
5-nitro-2-[3-(bromomethyl)-5-methyl-4H-1,2,4-triazol-4-yl]benzophenone;
3-(trifluoromethyl)-2'-fluoro-2-[3-(bromomethyl)-5-methyl-4H-1,2,4-triazol-4-yl]benzophenone;
2'-fluoro-2-[3-(bromomethyl)-5-ethyl-b 4H-1,2,4-triazol-4-yl]benzophenone;
2'-fluoro-2-[3-(iodomethyl)-5-ethyl-4H-1,2,4-triazol-4-yl]benzophenone;
3'-fluoro-2-[3-(bromomethyl)-5-propyl-4H-1,2,4-triazol-4-yl]benzophenone;

5-chloro-2-[3-(bromomethyl)-5-isopropyl-4H-1,2,4triazol-4-yl]benzophenone;

4-nitro-2'-chloro-2-[3-(bromomethyl)-5-ethyl-4H-1,2,4-triazol-4-yl]benzophenone;

6-bromo-2'-chloro-2-[3-(iodomethyl)-5-ethyl-4H-1,2,4-triazol-4-yl]benzophenone;

2',5-dichloro-2-[3-(iodomethyl)-5-propyl-4H-1,2,4-triazol-4-yl]benzophenone;

5-fluoro-2-[3-(chloromethyl)-5-methyl-4H-1,2,4-triazol-4-yl]benzophenone;

5-(trifluoromethyl)-2-[3-(chloromethyl)-5-methyl-4H-1,2,4-triazol-4-yl]benzophenone;

2-[3-(chloromethyl)-5-methyl-4H-1,2,4-triazol-4-yl]benzophenone;

and the like.

I claim:

1. 5-Chloro-2-[3-(bromomethyl)-5-methyl-4H-1,2,4-triazol-4-yl]benzophenone.

2. 5-Chloro-2-[3-(chloromethyl)-5-methyl-4H-1,2,4-triazol-4-yl]benzophenone.

3. 5-Chloro-2-[3-(iodomethyl)-5-methyl-4H-1,2,4-triazol-4-yl]benzophenone.

4. 2',5-Dichloro-2-[3-(bromomethyl)-5-methyl-4H-1,2,4-triazol-4-yl]benzophenone.

5. 5-Chloro-2',6'-difluoro-2-[3-(bromomethyl)-5-methyl-4H-1,2,4-triazol-4-yl]benzophenone.

* * * * *